United States Patent [19]

Dietz

[11] Patent Number: 5,585,117
[45] Date of Patent: Dec. 17, 1996

[54] USE OF A MIXTURE OF CALCIUM HYDROXIDE AND OLEUM PEDUM TAURI FOR COLLAGEN REFORMATION IN VIVO

[76] Inventor: Georg Dietz, Mauerkircher Str. 120, 81925 München, Germany

[21] Appl. No.: 569,831

[22] Filed: Dec. 7, 1995

Related U.S. Application Data

[63] Continuation of Ser. No. 160,855, Dec. 3, 1993, abandoned.

[30] Foreign Application Priority Data

Dec. 3, 1992 [DE] Germany .................. 42 40 713.3

[51] Int. Cl.⁶ .................. A61K 33/08; A61K 35/12
[52] U.S. Cl. .................. 424/693; 424/522; 424/526; 424/689; 514/547; 514/557; 514/558; 514/560; 128/DIG. 8
[58] Field of Search .................. 424/693, 522, 424/689, 526; 128/DIG. 8; 514/547, 557, 558, 560

[56] References Cited

U.S. PATENT DOCUMENTS

| | | | |
|---|---|---|---|
| 4,311,528 | 1/1982 | Dietz et al. | 106/35 |
| 5,236,496 | 8/1993 | Shibuya et al. | 424/692 |

OTHER PUBLICATIONS

Martindale The Extra Pharmacopoeia, 28th edition, The Pharmaceutical Press (London), 1982, pp. 1063–1064.
The Merck Index, 11th ed., Merck & Co., Inc., NJ, 1989, p. 1139.

*Primary Examiner*—John Pak
*Attorney, Agent, or Firm*—Breiner & Breiner

[57] ABSTRACT

A method of promoting collagen reformation in vivo comprises applying a mixture of calcium hydroxide and oleum pedum tauri, optionally with pharmaceutically tolerable auxiliaries, to the tissue in need of collagen reformation. Enhanced bone healing results, following general surgery, dental surgery, tooth implantation etc.

3 Claims, 9 Drawing Sheets

○ CALCIUM HYDROXIDE IN AQUEOUS SUSPENSION

● CALCIUM HYDROXIDE/OLEUM PEDUM TAURI MIXTURE

Fig.5

LABELING I

Heat-denatured tissue

LABELING I

Vital tissue

Fig. 6

LABELING II

Calcium hydroxide/oleum pedum tauri mixture

LABELING II

Aqueous calcium hydroxide suspension

Fig. 7

LABELING III

Calcium hydroxide/oleum pedum tauri mixture

LABELING III

Aqueous calcium hydroxide suspension

Fig. 8

LABELING VII

Aqueous calcium hydroxide suspension

LABELING VII

Barium sulfate-containing mixture of calcium hydroxide and oleum pedum tauri

CALCIUM HYDROXIDE/OLEUM PEDUM TAURI MIXTURE

Fig.11

BARIUM SULFATE-CONTAINING CALCIUM HYDROXIDE/OLEUM PEDUM TAURI MIXTURE

Fig. 12

USE OF A MIXTURE OF CALCIUM HYDROXIDE AND OLEUM PEDUM TAURI FOR COLLAGEN REFORMATION IN VIVO

This is a continuation of application Ser. No. 08/160,855 filed on Dec. 3, 1993 now abandoned.

BACKGROUND OF THE INVENTION

The invention relates to a use of a mixture of calcium hydroxide and oleum pedum tauri and to the promotion of collagen reformation in vivo.

Bone consists to about 60% of mineral substance (hydroxyapatite, calcium phosphate) and to about 40% of organic material, in particular collagen. The metabolism of bone is mainly determined by the interplay of bone-synthesizing cells (osteoblasts) and bone-degrading cells (osteoclasts and osteocytes), the activities of which are in a balanced ratio in healthy bone.

Bone formation can be divided into two main phases, (a) the synthesis of organic tissue (collagen synthesis) and (b) the incorporation of mineral substance into the given organic matrix which follows and is mediated by so-called matrix vesicles.

The connective tissue protein collagen makes up the largest portion of the organic substance of the bone. The protein consists of three helically wound polypeptide chains, the amino acid composition of which can vary, which leads to a variety of individual types of collagen. An extremely high mechanical strength of the collagen fibers is common to all types of collagen. This strength is based on a variety of intra- and intermolecular bonds in the collagen fibers, which in this manner form the tight collagen fiber network of the connective tissue. Osseous tissue—as already mentioned—is formed into this network by incorporation of mineral substances (hydroxyapatite and calcium phosphate). Any bone synthesis as a result of growth or regeneration processes is preceded by collagen biosynthesis.

Up until now, in the case of bone traumas of any origin the bone reformation process was left to itself, if need be supported with antibiotics and corticoids, in order to prevent a possible risk of infection interfering with the healing process.

Several factors have also been described which can affect the formation and regeneration of bone. They are mainly physical factors (mechanical and electrical forces), hormones (for example parathyroid hormone, calcitonin, insulin, glucocorticoids, $1,25(OH)_2D3$) and an inexactly defined group of growth factors having protein character (osteoquinine, osteonectin, "insulin-like growth factors")—cf. S. Wallach, L. V. Avioli, J. H. Carstens jun "Factors in Bone Formation", Calcified Tissue International 45: 4–6 (1989). The influence of the hydrogen ion concentration (pH) on the metabolic processes in bone regeneration has still not been adequately investigated to date.

PRIOR ART

Barium sulfate-containing mixtures of calcium hydroxide and oleum pedum tauri have been used in dental medicine as a root-filling paste (German Patent 2,932,738). Mixtures of carboxylate cement, calcium hydroxide and oleum pedum tauri have likewise already been used in dental medicine as temporary fixatives for provisional tooth stump maskings (German Patent 3,413,864). The object of the calcium hydroxide in the former case is to change the acidic medium in the root canals into alkaline medium, resulting in the elimination of inflammations and gradual formation of a hard tissue barrier. In the latter case, the pulpitis prophylactic action of calcium hydroxide is utilized. The oleum pedum tauri is used in both cases as a pasting agent in order on the one hand to guarantee a simple and complete filling of the root canals with the actual active compound calcium hydroxide (and the contrast agent barium sulfate) and on the other hand to slow down the hardening of the temporary fixative for provisional tooth stump maskings so much that the calcium hydroxide can still advance through the fine dentinal tubtiles to the pulp and can display its action there. In both literature references, not the slightest indication is found that the mixture of calcium hydroxide and oleum pedum tauri is able to induce collagen reformation on a huge scale as a prerequisite for bone regeneration.

SUMMARY OF THE INVENTION

It has now surprisingly been shown that when using a mixture of calcium hydroxide and oleum pedum tauri and, if desired, pharmaceutically tolerable auxiliaries in or on bone traumas, a collagen reformation which is rapid and significant in its extent takes place in vivo.

In the mixture of calcium hydroxide and oleum pedum tauri according to the invention, the ratio of calcium hydroxide to oleum pedum tauri can be about 2:1 to about 1:2, preferably about 1:1. Deviation from the preferred mixing ratio may be necessary owing to the specific conditions of the wound trauma.

If the mixture of calcium hydroxide and oleum pedum tauri according to the invention is to have a particularly soft and smooth consistency, white petroleum jelly can also be incorporated into it.

Although the bone healing or regeneration process does not customarily need to be monitored by X-ray, this may be indicated in some cases. In this case, barium sulfate is additionally incorporated into the mixture of calcium hydroxide and oleum pedum tauri according to the invention as an X-ray contrast agent. As, however, the barium sulfate—as will additionally be shown—allows the collagen reformation to take place somewhat more weakly, if required just sufficient barium sulfate is added to the mixture according to the invention such that the mixture is just visible by X-ray.

DETAILED DESCRIPTION OF THE INVENTION

The essential constituents of the mixture according to the invention, namely calcium hydroxide and oleum pedum tauri, should be mixed more or less immediately before application to a or in a bone trauma to avoid hydrolysis of the oleum pedum tauri. This can be carried out, for example, by separate packing of the two constituents in so-called shake capsules and combination of the two constituents immediately before use.

The application of the mixture according to the invention to or in the bone trauma can be carded out-depending on its consistency—by means of syringes, spatulas or brushes.

There are numerous possibilities of use for the mixture according to the invention in general surgery and dental surgery, orthopedics, implantology, traumatology and the like, as the mixture according to the invention can be applied to or in bone tissue traumas, such as fracture surfaces, drillings, cavities and the like and immediately induces in vivo collagen reformation at the particular application site.

As it is known that work is carried out in some appropriate medical disciplines using metallic fixatives, it is recommended in this case to fill the drilling prepared for the insertion of the fixative with the mixture according to the invention before the insertion of the fixative and only then to introduce the fixative. It is possible by this means to counter the primary bone loss which is unavoidable with measures of this type and thereby to accelerate the adaptation or adjustment of the fixative to or on the surrounding osseous tissue and to accelerate the fixing of the fixative itself by the osseous tissue.

Excess mixture does not otherwise interfere in this case, as it is either squeezed out again during insertion of the fixative into the drilling filled with the mixture or diffuses into the spongiosa.

It must be obvious that the mixture according to the invention or its constituents must be both packed and applied under sterile conditions.

In the most highly surprising manner, it has additionally been shown that the mixture according to the invention also counteracts an inflammatory reaction caused by the bone trauma or makes this rapidly subside without antibiotic and/or corticoid assistance. Its simple composition and marked activity in in vivo collagen reformation with simultaneous inhibition of inflammation make the mixture according to the invention a valuable composition in bone traumatology.

The following examples are intended to illustrate the invention in greater detail.

EXAMPLE 1

A) First, the interaction between the mixture of calcium hydroxide and oleum pedum tauri according to the invention and tissue should be elucidated. Thus, data about the distribution of the mixture of calcium hydroxide and oleum pedum tauri according to the invention in osseous tissue are a requirement in order to be able to put forward hypotheses about a possible mechanism of action of the medicament. Experiments on tissue cultures are therefore more useful than those on cell cultures, as it is only possible to study cell-cell interactions in a tissue culture.

1. Material and methods 1.1 Tissue material

Human osseous tissue which was obtained in osteotomies was made available by clinics.

Embryonic osseous tissue was obtained from chicken embryos (Gallus domesticus) 10 to 17 days old.

1.2 Tissue culture

Immediately after removal, the tissue was transferred to the transport medium. Bone fragments about 2 mm$^3$ in size were prepared under sterile conditions and, after determination of the weight, employed directly for the experiments.

Earl's modification of the minimal essential medium (MEM) according to Eagle containing 20 mM Hepes buffer was used for tissue culture.

Before the start of the experiments, 4 % fetal calf serum and 1% antibiotic solution (penicillin/streptomycin/amphotericin B) and, for the labeling experiments, additionally 1 mM beta-aminopropionidyl, 2 mM Na ascorbate and 2 to 10 µCi of isotope ($^{14}$C-proline) are added to the medium. Culturing is carried out in 25 ml Erlenmeyer flasks at 37° C. in a shaking water bath at the lowest rate.

1.3 Determination of the respiratory activity

The respiratory activity is a sensitive marker for the metabolic activity of the tissue. Even the smallest changes in the physiological condition of the tissue are reflected in a measurable change in the respiratory activity.

A Clark sensor (platinum/silver electrodes in saturated potassium chloride solution) was used to determine the respiratory activity. When a voltage of 0.8 V is applied to the electrode, the oxygen reduction current is directly proportional to the oxygen partial pressure in the measuring solution (culture medium). Addition of $O_2$-saturated medium when the oxygen partial pressure falls below a certain value and data analysis are carried out by computer control.

Figure 1:
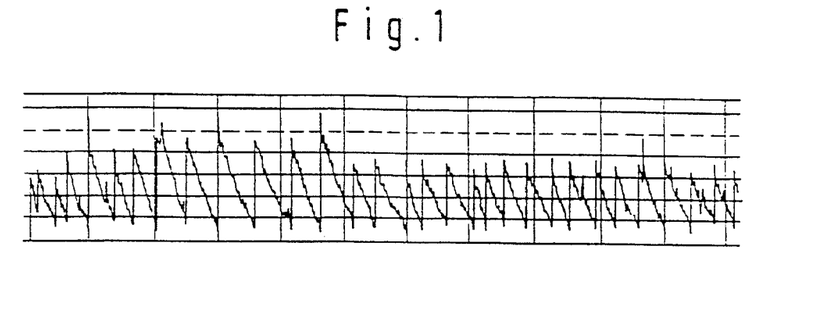
FIG. 1 shows a typical respiration curve for osseous tissue.

Osseous tissue typically has a respiratory activity of 2–3 µl of $O_2 \cdot min^{-1} \cdot g^{-1}$. The respiratory activity is thus in the range of the respiratory activity of resting muscle tissue according to order of magnitude. A typical respiration curve for osseous tissue is shown in FIG. 1. The sawtooth-like course of the respiration curve according to FIG. 1 results from the fact that when the $O_2$ partial pressure in the measuring solution falls below a certain value, fresh, $O_2$-saturated medium is added.

Figure 2:
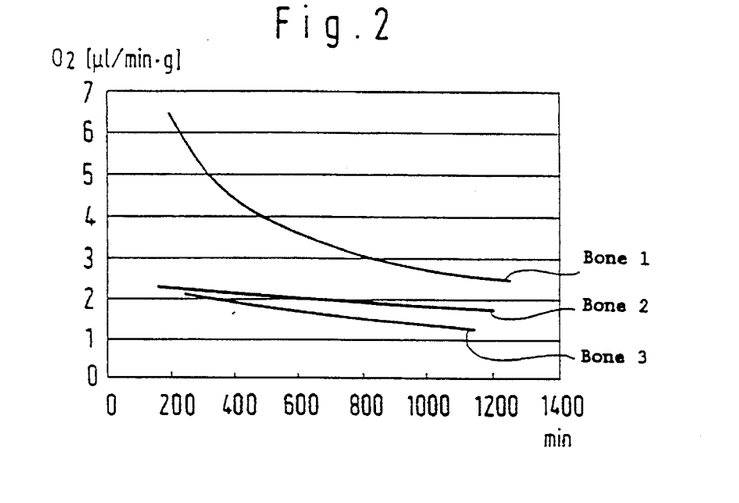
FIG. 2 shows average $O_2$ consumption values from three measurements.

FIG. 2 shows average $O_2$ consumption values from the measurements. The oxygen consumption of embryonic osseous tissue (Gallus domesticus) was determined in a tissue culture with the aid of the Clark sensor. The oxygen consumption is between 3 and 5 µl of $O_2 \cdot min^{-1} \cdot g^{-1}$. The respiratory activity decreases in the course of time by about 50%, which is perfectly normal for tissue cultures.

1.4 Enzyme tests

Alkaline phosphatase is an enzyme which is connected closely with the mineralization of osseous tissue. This enzyme has already been characterized for a relatively long time; additional discussion is taking place about the function of the enzyme in mineralization. As there is a close relationship between the osteoblast activity and the activity of alkaline phosphatase, alkaline phosphatase can be regarded as a marker of osteoblast activity. During skeletal growth in adolescence, during bone regeneration and during disorders of bone metabolism, increased activity values of alkaline phosphatase are found in the blood serum.

The activity of alkaline phosphatase was determined in a crude extract. For this purpose, 500 mg of tissue were treated with 1 ml of disruption buffer and comminuted using a knife. 500 mg of grinding beads were then added and the mixture was disrupted for 20 min. After centrifugation, the crude extract was employed for the measurements.

Alkaline phosphatase is detected using the conversion of p-nitrophenyl phosphate to nitrophenol and phosphate. The nitrophenol formed during the hydrolysis is yellow and can therefore be detected in a photometer at a wavelength of 410 nm.

Figure 3:
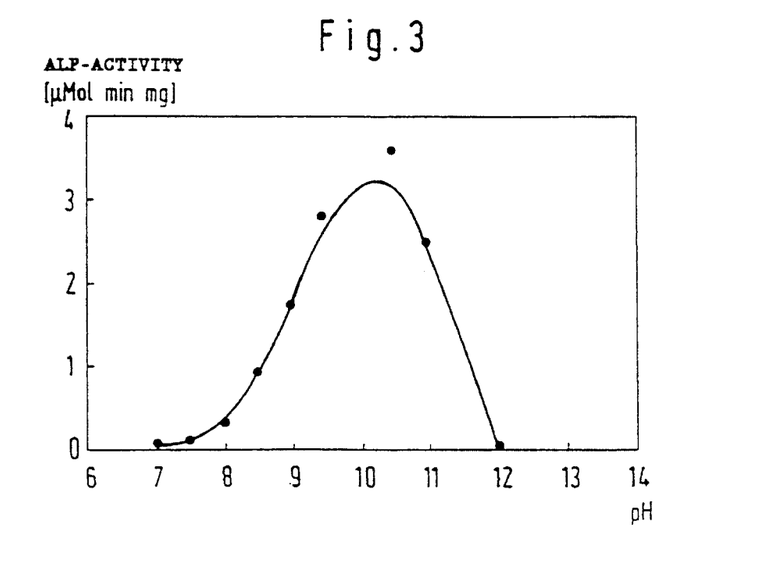
FIG. 3 shows the pH dependence of the activity of alkaline phosphatase.

FIG. 3 shows the pH dependence of the activity of alkaline phosphatase. The activity of alkaline phosphatase from bone was determined using the conversion of p-nitrophenyl phosphate. The activity maximum was at pH 10.5. At a physiological pH of 7, alkaline phosphatase only has about 1% of the maximum activity.

1.5 pH Determination

A mixture of calcium hydroxide and oleum pedum tauri according to the invention or an aqueous calcium hydroxide suspension was covered with 30 ml of imidazole/HCl buffer (1 mM, pH 7), after which the pH in the solution was monitored continuously with the aid of a pH electrode.

Figure 4:
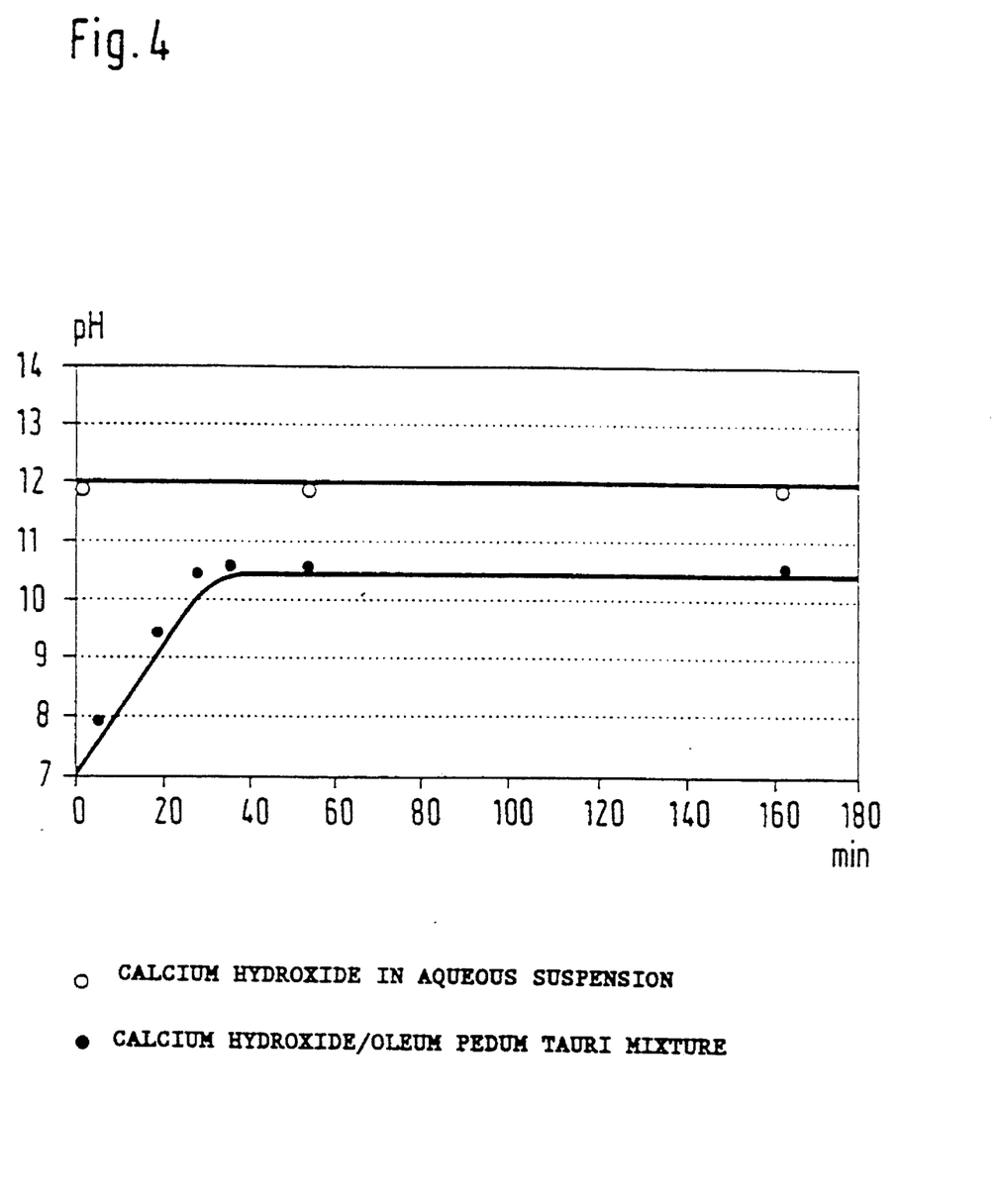
FIG. 4 shows the pH change with aqueous calcium chloride and with the mixture used in the invention.

During these measurements, it was seen that calcium hydroxide in oleum pedum tauri has fundamentally different properties to calcium hydroxide in aqueous suspension. FIG. 4 shows that an aqueous calcium hydroxide suspension causes an immediate pH jump to pH 12, and that in the calcium hydroxide/oleum pedum tauri mixture according to the invention a slower increase takes place up to a pH of greater than 10.

1.6 Collagen determination

The bulk of the organic substance in bone consists—as already mentioned—of collagen, a connective tissue protein. Growth and regeneration processes of the bone are associated with de novo collagen synthesis. Subsequently to the synthesis, further intra- and extracellular collagen processes take place. Using radioactive collagen precursors ($^{14}C$-proline), it is possible to quantify the collagen synthesis rate in a tissue culture exactly. It is thus possible to record the effect of medicaments on collagen synthesis qualitatively and quantitatively.

The total collagen content is determined by the so-called hydroxyproline test. The amino acid hydroxyproline occurs mainly in collagen; the hydroxyproline content in foreign proteins can be neglected. After release of the amino acids from the proteins by hydrolysis (16 h at 116° C., 22 % HCl), the total hydroxyproline content in the test mixture after chemical modification (oxidation of the 4-hydroxyproline to pyrrole) is quantified by a specific color reaction with p-dimethylaminobenzaldehyde.

1.7 Determination of the collagen synthesis rate

Collagen in tissue and medium is obtained according to the method of Miller and Roths (cf. E. J. Miller and R. H. Roths "Methods in Enzymol." 82:33 (1982)) modified by Proff (1991). Collagen is quantified via SDS gel electrophoresis and subsequent scintillation measurement (determination of the specific radioactivity) by means of several precipitation steps with subsequent centrifugation. To calculate the de novo synthesis rate, the proportion of collagen determined by the incorporation of $^{14}C$-proline, relative to the total collagen content which is determined by the hydroxyproline test, is determined.

By quantification of collagen biosynthesis, it is possible to investigate the effect of calcium hydroxide preparations on bone formation.

The quantification of collagen biosynthesis is carried out—as indicated in 1.7—by the technique of radioactive labeling of the collagen. One constituent of the collagen fiber is the amino acid proline. An exactly defined amount of $^{14}C$-labeled proline is added to the culture medium. This proline is incorporated into the proteins newly synthesized during the incubation of the tissue. After the separation of the collagen from other proteins, it is possible by determination of the specific radioactivity to make an exact quantitative statement about the de novo synthesis rate of the collagen.

The collagen is isolated by means of several precipitation steps with subsequent centrifugation and SDS gel electrophoresis. In the specific precipitation of the collagen, the collagen fibers are separated from other proteins by setting a suitable salt concentration, under which non-collagen proteins to a large extent remain in solution, but the collagen deposits from the solution as a precipitate, by addition of sodium chloride. The collagen is sedimented by means of subsequent centrifugation. Proteins are separated from one another as a function of size in the SDS gel electrophoresis. In an electric field, the proteins migrate through a matrix of a highly crosslinked polymer (acrylamide). Small proteins migrate rapidly through this matrix, as this offers a low resistance to the molecules; large proteins migrate more slowly, as their mobility is strongly hindered by the matrix. After staining, proteins are visible in this gel as so-called "bands". In this manner, proteins can be identified by their size by means of internal size standards.

By cutting out bands which are of interest from the gel, the proteins are accessible for further analysis, for example radioactivity measurement.

Extraction of collagen

Tissue culture (cf. 1.2) was stopped by addition of 3% acetic acid. Collagen which had gone into solution was precipitated overnight at 4° C. by means of 2 M sodium chloride and then recovered by centrifugation (1 h, 24,000 g, 4° C.). The sediment was taken up in 10 ml of 3% strength acetic acid. Newly synthesized collagen, which is located within the tissue block, is also included in the analysis by mechanical disintegration of the tissue blocks. Tissue residues were removed by centrifugation (1 h, 45,000 g, 4° C.). The collagen in the supernatant was recovered by a further precipitation (2 M NaCl, 4° C.) and centrifugation (1 h, 100,000 g, 4° C.). After solubilization, the sediment was separated by gel electrophoresis. To check the separation of the proteins, they were stained in the gel.

After the run, the gel was cut up into 5 mm wide strips transversely to the direction of the run, and the gel fragments were transferred to scintillation containers and counted in a scintillation counter.

B. FIGS. 5 to 9 show the result of a few selected experiments.

The radioactivity distribution in the gel is shown on the figures. Collagen, as a relatively large protein, can be found in the area 2 cm removed from the start.

A specific radioactive band can be related to the collagen band which is detectable by Coomassie staining.

Figure 5:
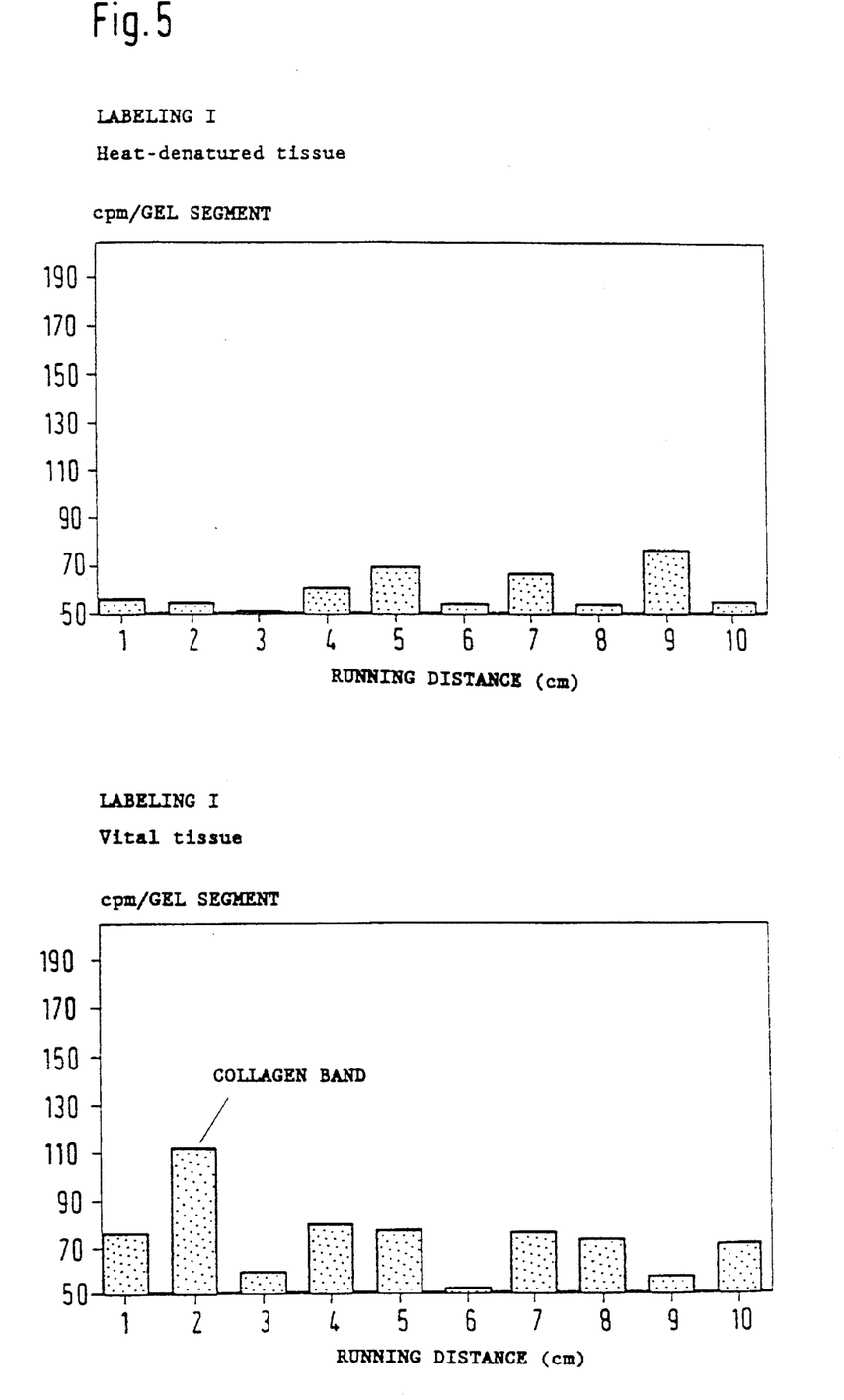
FIGS. 5 to 9 are graphs of collagen growth (expressed as radioactivity (cpm) per gel segment) in respective experiments.
Figure 6:
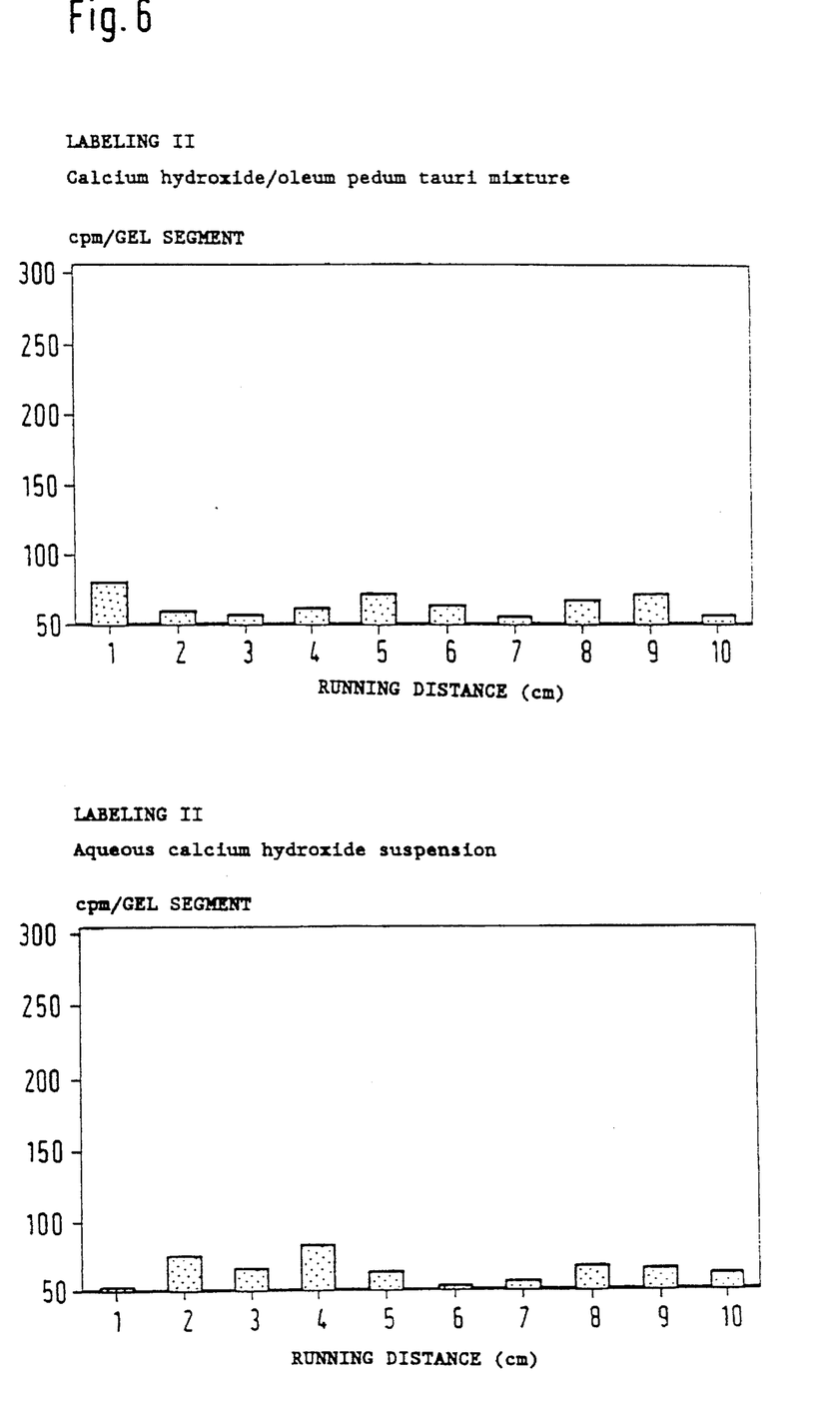

The comparison between a vital and a heat-denatured tissue is shown in FIG. 5.

FIG. 5 Labeling I, head of the femur, spongiosa, male, 45 years old; Difference in the collagen synthesis capacity between vital and heat-denatured tissue (CPM: counts per minute). The distribution of the radioactivity in the gel is shown here. The collagen band is located in an area which is about 2 cm removed from the start. A collagen band occurs only in vital tissue, i.e. the radioactivity to be detected in the gel corresponds to de novo synthesis of the collagen during the incubation.

The vital tissue shows a detectable collagen synthesis capacity; the destroyed tissue on the other hand no longer shows any metabolic activity. This shows that the radioactive collagen detected can in fact be attributed to de novo collagen synthesis in the tissue culture and not to a non-specific binding of radioactive proline to proteins of the osseous tissue. A comparable amount of tissue material was employed for all experiments (about 100 mg).

Further radioactively labeled bands of smaller size are detectable, it being possible for these to be degradation products of collagen. The degradation of collagen in tissue culture is to be observed in particular in labeling experiments over an incubation period of 4 days. To a smaller extent, radioactively labeled proline which it was not possible to remove completely by the precipitations is also present in the gel.

FIGS. 6 to 9 show the results of some selected labeling experiments under the effect of calcium hydroxide. Collagen synthesis was determined in the unstimulated state (control) under the effect of various calcium hydroxide/oleum pedum tauri mixtures and of an aqueous calcium hydroxide preparation. Identical tissue was employed in each series of experiments, i.e. tissue portions from the same body region of the donor. In detail, the figures show the following FIG. 6 Labeling II, head of the femur, spongiosa, male, 75 years old; Labeling experiment under the effect of a calcium hydroxide/oleum pedum tauri mixture and of an aqueous calcium hydroxide suspension. The tissue is only slightly metabolically active. Tissue from patients of relatively high age (over 65 years) always shows greatly decreased collagen synthesis.

Figure 7:
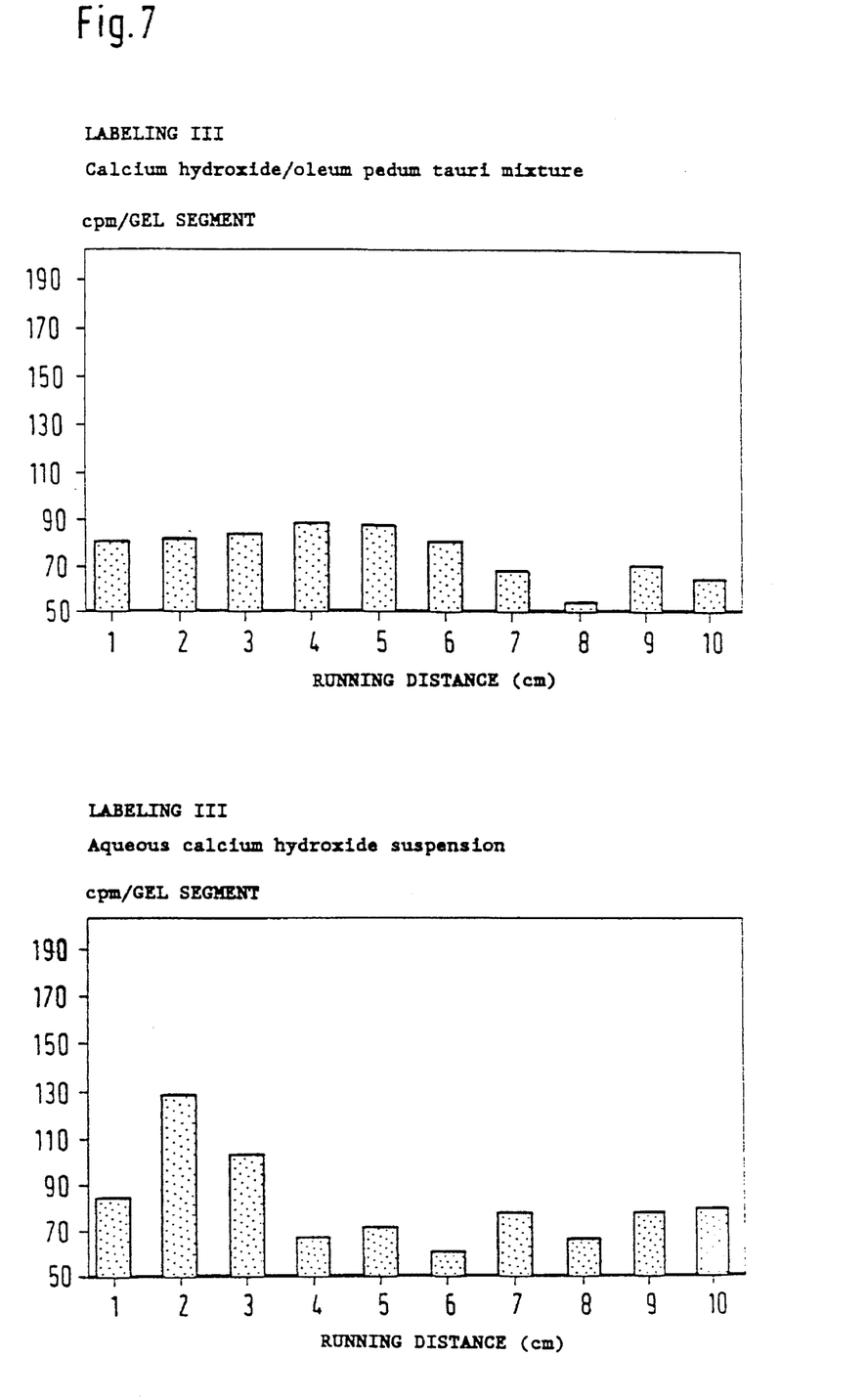

FIG. 7 Labeling III, head of the femur, spongiosa, male, 53 years old; Labeling experiment under the effect of a calcium hydroxide/oleum pedum tauri mixture and of an aqueous calcium hydroxide suspension. The incubation with the calcium hydroxide/oleum pedum tauri mixture does not show any negative effect on the collagen synthesis; incubation with an aqueous calcium hydroxide suspension led to necrosis of the tissue.

Figure 8:
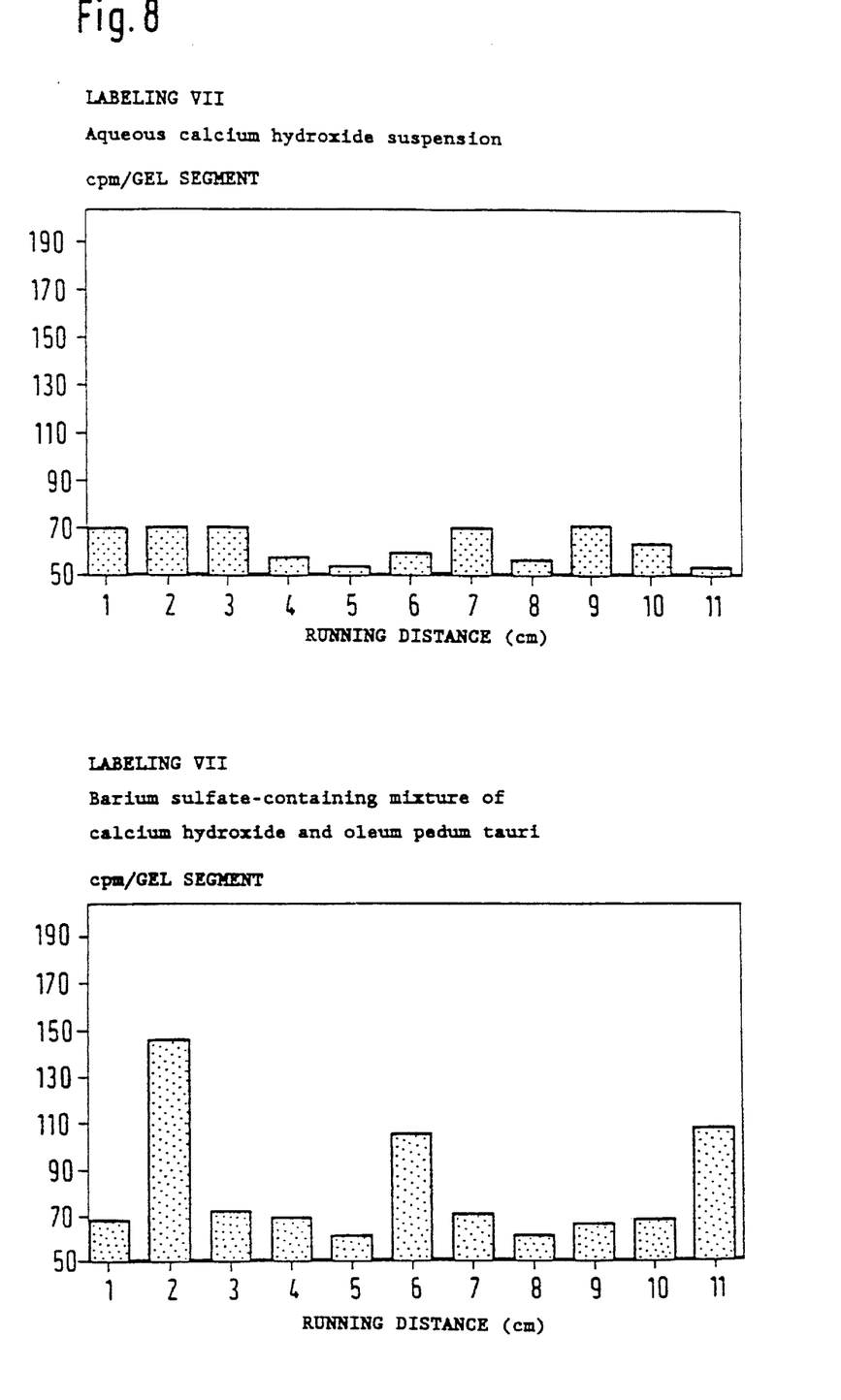

FIG. 8 Labeling VII, head of the tibia, spongiosa, female, 51 years old; Labeling experiment under the effect of a barium sulfate-containing calcium hydroxide/oleum pedum tauri mixture and of an aqueous calcium hydroxide suspension. As in the incubation as in FIG. 7, here too a collagen synthesis capacity is only detectable when using the calcium hydroxide/oleum pedum tauri mixture.

Figure 9:
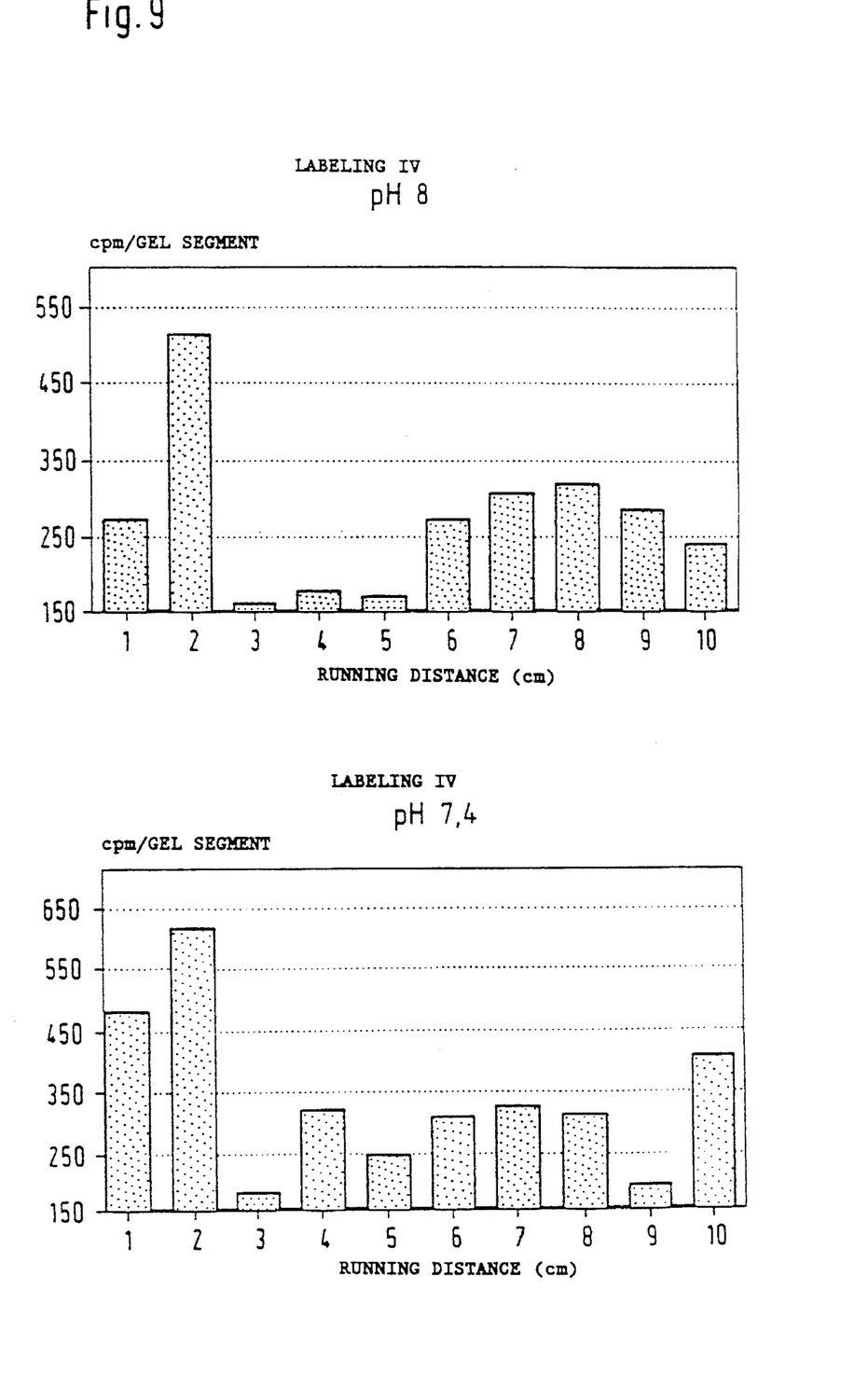

FIG. 9 Labeling IV, head of the tibia, spongiosa, male, 63 years old; Distribution of the radioactivity in the gel after incubation at pH 7.4 and 8.0. Collagen synthesis is not significantly changed, which shows the tolerance of the osseous tissue to moderate basification.

Figure 12:
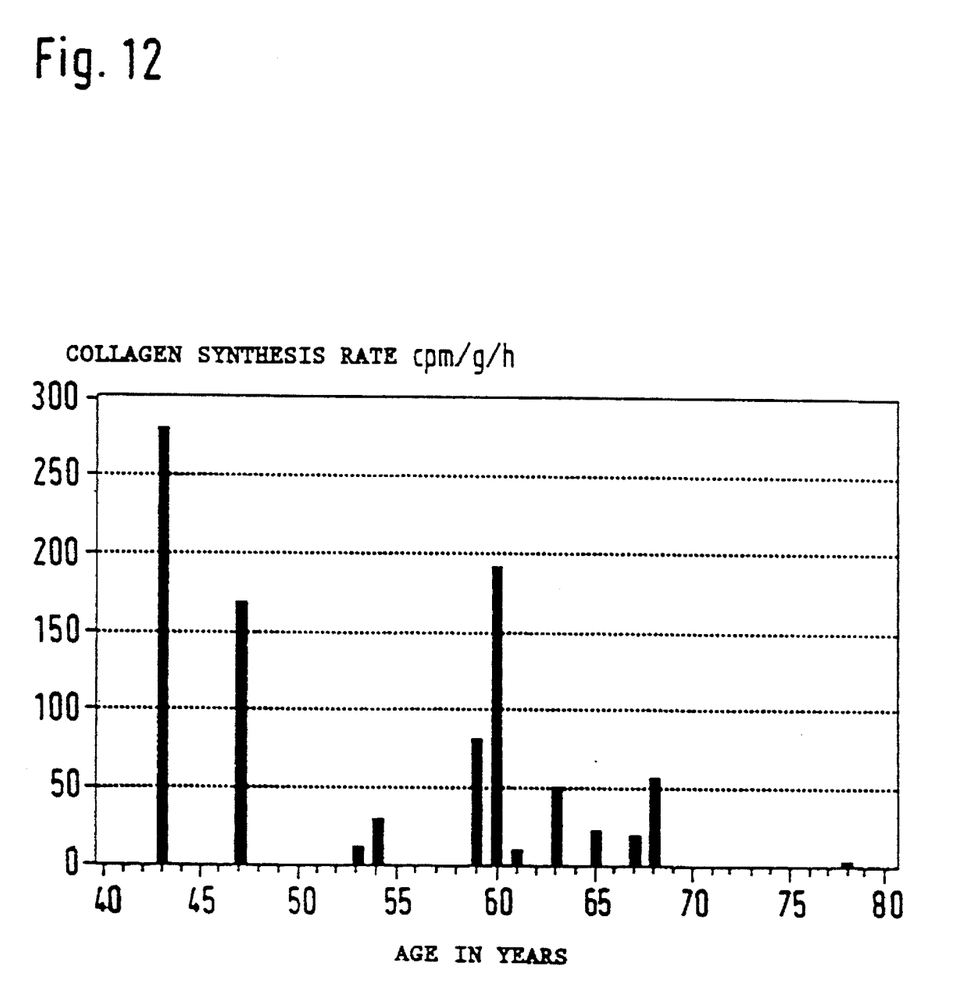
FIG. 12 shows the rate of collagen synthesis in patients of differing ages.

The following statements can be made from the labeling experiments: The metabolic activity of the tissue is strongly age-dependent. The labeling experiments in which tissue of relatively old patients was employed show a low collagen synthesis activity (FIG. 6), but the stimulating action of mixtures of calcium hydroxide and oleum pedum tauri according to the invention occurs not only in young, but also in relatively old patients (FIG. 12).

Incubation with an aqueous calcium hydroxide suspension (FIGS. 6 to 8) leads in each case to necrosis of the tissue. Collagen synthesis cannot be detected. This is attributable to the strong pH rise in the tissue culture. After incubation for three days, the culture medium has assumed a pH of 12.

De novo collagen synthesis is to be observed under the effect of the mixture of calcium hydroxide and oleum pedum tauri according to the invention. The pH of the medium after the incubation never exceeds a value of 10.5. Significant differences between various calcium hydroxide/oleum pedum tauri mixtures (FIGS. 7 and 8) did not occur if a collagen formation rate decreased by about 10% is also to be detected in the barium sulfate-containing mixture. Even in the latter case, the greatest amount of radioactively labeled proteins is to be found in the collagen band.

The tolerance of the osseous tissue to weakly alkaline pH values is revealed by a parallel experiment to the experiment illustrated in FIG. 5. In the parallel experiment, the physiological Hepes buffer of the culture medium (pH 7.4) was replaced by a bicarbonate buffer (pH 8.0). In this case, it emerged that the basification of the culture medium to pH 8.0 resulted in no measurable difference in the collagen synthesis capacity compared to pH 7.4. From pH 8.5, increased collagen reformation is no longer to be observed compared to spontaneous collagen reformation.

The findings obtained up to now, that aqueous calcium hydroxide suspensions bring about necrosis of the tissue and do not stimulate de novo collagen synthesis as a result of their strongly basifying action, and that, on the other hand, mixtures of calcium hydroxide and oleum pedum tauri have a significant stimulating action on de novo collagen synthesis, were corroborated by further experiments. These experiments were carried out as already described.

Figure 10:
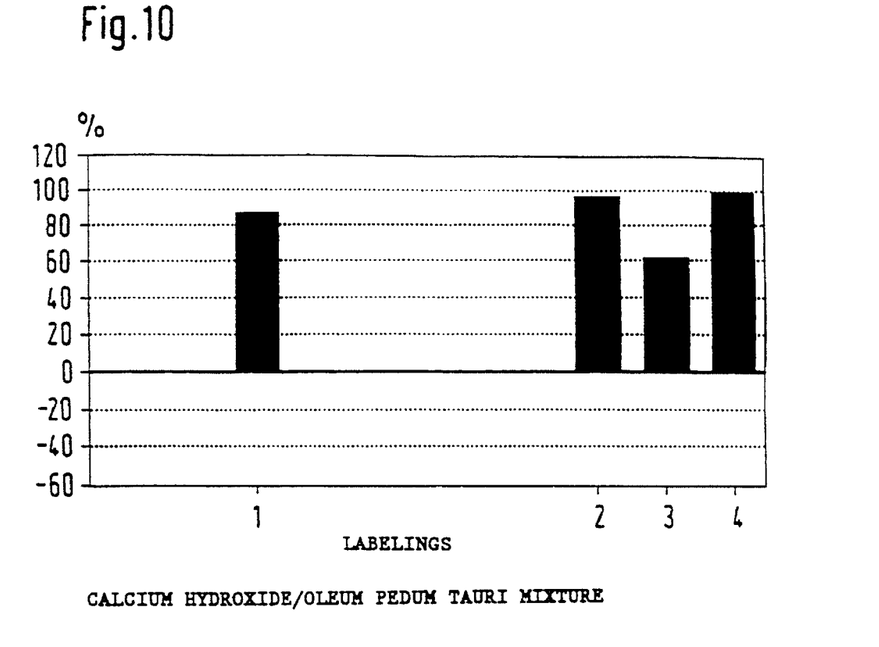
FIGS. 10 and 11 are graphs of collagen growth, expressed as a percentage of growth in the control experiments, in further experiments.
Figure 11:
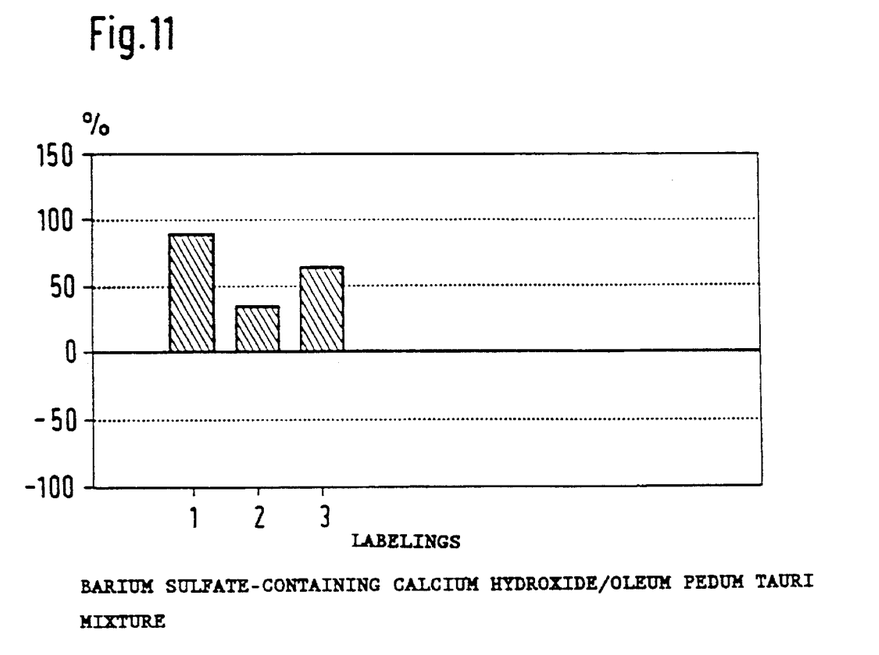

FIGS. 10 and 11 show the amount of newly synthesized collagen in the experimental batches containing a calcium hydroxide/oleum pedum tauri mixture in comparison to control batches without this mixture. The difference in the amount of newly synthesized collagen in the control and in the experimental batch is expressed in percent. 0% denotes no increased amount of newly synthesized collagen compared to the control, experimental batch containing the mixture 100% denotes a collagen reformation under the effect of the mixture increased twice compared to the control. It emerges from FIG. 10 that the collagen synthesis compared to the control is increased by between 60 and 90% in the four experiments under the effect of a calcium hydroxide/oleum pedum tauri mixture. This increase is significant, as experimentally related variations in the collagen synthesis capacity are in the range from 10 to 20%, but the increases determined tinder the effect of calcium hydroxide/oleum pedum tauri mixture are between 60 and 90%.

FIG. 11 shows the results relating to the collagen synthesis capacity under the effect of a barium sulfate-containing mixture of calcium hydroxide and oleum pedum tauri. If even here the collagen synthesis capacity compared to the mere mixture of calcium hydroxide and oleum pedum tauri is somewhat reduced, the presence of barium sulfate may be desired in spite of this, in particular if the calcium hydroxide preparation is to be visible by X-ray. Using such a preparation, the changes accompanying the treatment and absorptions of the medicament can be monitored in the X-ray image.

Results on clinical application of the mixture according to the invention after cutting of bone during root apex resection or in the preparation of implant beds.

EXAMPLE 2

If the bone defects as a result of cutting are provided with the mixture according to the invention, there is protection against infection, inhibition of inflammation (the normal reactive inflammation after bone traumatization) and a strong osteoregenerating stimulus. In the case of 8 teeth having a root apex resection and the apical formation of a bone wound of 0.5 to 1 cm diameter, the application of the mixture according to the invention led to a strong decrease or freedom from post-operative pains. 3 cases were completely pain-free: 4 cases only showed slight symptoms on the first day after the intervention and one case had medium pains only on the 2nd day after the intervention. The normal severe swelling to be expected after cutting of bone of this type was in one case not present at all, and in 6 cases it was only slightly present on the 2nd day. Only one case showed severe swelling on the 2nd day. With respect to post-operative inflammation, 2 cases showed no symptoms of inflammation at all; 3 cases had a slight inflammation on the 1st or 2nd or 3rd day. 3 cases showed a slight to medium inflammation after the 1st or 2nd day. In no case was there the severe post-operative inflammation customarily to be observed.

EXAMPLE 3

7 bone drillings were cut in the upper jaw in the case of a 50-year old toothless female patient to admit implants. The bone drillings were 1.5 to 2 cm deep and about 3 mm wide. The bone drillings were filled with the mixture according to the invention before screwing in the implants. The extremely surprising result was that the female patient needed no pain tablets on the next day after the intervention, and the swelling was minimal. The fact is particularly noticeable that after 2 weeks the reactive osteolysis rings around the implants to be expected in the X-ray image were completely missing. This means that even after 2 weeks an osteointegration of the implants is to be observed, which is normally to be expected only in 5–6 months. The X-ray image to be observed 2 weeks after the cutting of the bone corresponds to 90% to the X-ray result to be expected after 6 months.

The invention has been described in detail with particular reference to preferred embodiments thereof but it will be understood that variations and modifications can be effected without departing from the spirit and scope of the invention.

I claim:

1. A method of promoting collagen reformation comprising applying to or in a site of bone trauma a mixture of calcium hydroxide, oleum pedum tauri and white petroleum jelly, wherein (i) the white petroleum jelly is present in an amount sufficient to provide said mixture with a soft and smooth consistency, and (ii) said mixture is applied in an amount sufficient to promote collagen reformation.

2. The method of claim 1 wherein the volume ratio of calcium hydroxide:oleum pedum tauri is from about 2:1 to about 1:2.

3. The method of claim 2 wherein said ratio is about 1:1.

* * * * *